(12) United States Patent
Foley

(10) Patent No.: US 6,562,073 B2
(45) Date of Patent: May 13, 2003

(54) SPINAL BONE IMPLANT

(75) Inventor: Kevin T. Foley, Germantown, TN (US)

(73) Assignee: SDGI Holding, Inc., Wilmington, DE (US)

(*) Notice: Subject to any disclaimer, the term of this patent is extended or adjusted under 35 U.S.C. 154(b) by 0 days.

(21) Appl. No.: 09/777,702

(22) Filed: Feb. 6, 2001

(65) Prior Publication Data

US 2002/0107571 A1 Aug. 8, 2002

(51) Int. Cl.$^7$ .................................................. A61F 2/44
(52) U.S. Cl. ................................. 623/17.11; 623/17.16
(58) Field of Search ............................ 623/17.11, 17.16

(56) References Cited

U.S. PATENT DOCUMENTS

| | | |
|---|---|---|
| 4,349,921 A | 9/1982 | Kuntz |
| 4,599,086 A | 7/1986 | Doty |
| 4,627,853 A | 12/1986 | Campbell et al. |
| 4,892,545 A | 1/1990 | Day et al. |
| 4,946,378 A | 8/1990 | Hirayama et al. |
| 5,011,484 A | 4/1991 | Breard |
| 5,053,049 A | 10/1991 | Campbell |
| 5,092,866 A | 3/1992 | Breard et al. |
| 5,092,877 A | 3/1992 | Gendler |
| 5,180,393 A | 1/1993 | Commarmond |
| 5,423,816 A | 6/1995 | Lin |
| 5,458,641 A | 10/1995 | Ramirez Jimenez |
| 5,562,738 A | 10/1996 | Boyd et al. |
| 5,591,235 A | 1/1997 | Kuslich |
| 5,609,634 A | 3/1997 | Voydeville |
| 5,674,296 A | 10/1997 | Bryan et al. |
| 5,681,310 A | 10/1997 | Yuan et al. |
| 5,702,449 A | 12/1997 | McKay |
| 5,713,899 A | 2/1998 | Marnay et al. |
| 5,725,582 A | 3/1998 | Bevan et al. |
| 5,776,196 A | 7/1998 | Matsuaki |
| 5,899,939 A | 5/1999 | Boyce et al. |
| 5,916,267 A | 6/1999 | Tienboon |
| 5,989,289 A | 11/1999 | Coates et al. |
| 6,001,130 A | 12/1999 | Bryan et al. |
| 6,066,175 A | 5/2000 | Henderson et al. |
| 6,090,998 A | 7/2000 | Grooms et al. |
| 6,093,205 A | 7/2000 | McLeod et al. |
| 6,096,081 A | 8/2000 | Grivas et al. |
| 6,106,527 A | 8/2000 | Wu et al. |
| 6,120,503 A | 9/2000 | Michelson |
| 6,136,001 A | 10/2000 | Michelson |
| 6,156,037 A | 12/2000 | LeHuec et al. |
| 6,190,388 B1 | 2/2001 | Michelson et al. |
| 6,206,882 B1 | 3/2001 | Cohen |
| 6,235,059 B1 | 5/2001 | Benezech et al. |
| 6,306,170 B2 | 10/2001 | Ray |
| 6,325,827 B1 | 12/2001 | Lin |

FOREIGN PATENT DOCUMENTS

| | | |
|---|---|---|
| WO | WO 97/14377 | 4/1997 |
| WO | WO 97/37620 | 10/1997 |
| WO | WO 99/09914 | 3/1999 |
| WO | WO 99/21515 | 5/1999 |
| WO | WO 99/38453 | 8/1999 |
| WO | WO 99/38463 | 8/1999 |
| WO | WO 01/06933 | 2/2000 |
| WO | WO 00/40179 | 7/2000 |
| WO | WO/0040179 | 7/2000 |
| WO | WO 00/54821 | 9/2000 |
| WO | WO 00/74607 | 12/2000 |

Primary Examiner—David H. Willse
Assistant Examiner—Suzette J. Jackson
(74) Attorney, Agent, or Firm—Woodard, Emhardt, Naughton, Moriarty & McNett LLP

(57) ABSTRACT

Implantable devices useful for creating bony fusion particularly in intervetebral spinal fusion. The device is formed of bone and has a body portion with an upper flange member and an opposite lower flange member extending from the body portion. The upper and lower flange members are at least partially demineralized to create a flexible ligament extending from the body portion. In one application, the body portion is inserted into a disc space and the flexible ligament is secured to vertebrae on either side of the disc space. Techniques are also disclosed for making the implantable devices and for inserting the implantable device into an intervertebral disc space to promote interbody fusion.

34 Claims, 2 Drawing Sheets

SPINAL BONE IMPLANT

BACKGROUND OF THE INVENTION

The present invention relates to implantable spinal devices and methods for their use. More particularly, the present invention relates to interbody devices formed of bone that may be utilized in spinal fusions.

A variety of interbody implants are available for spinal fusion procedures. These implants have been manufactured of various materials including steel, titanium, composites, allograft, xenograft or other biocompatible materials, and have the necessary strength to prevent the disc space from collapsing before fusion has occurred. Other techniques for spinal fusion include the placement of bone graft material in the disc space along with a plate or rod construct that spans the affected disc space. One disadvantage to the above devices is that once fusion has occurred, the implants and hardware used to maintain the stability of the segment is unnecessary and remains in the body as a foreign object.

Other types of implants have been developed from biocompatible metals which incorporate threads on the outer surface of the implant that retain the implant in the disc space after it is threaded therein. Still other implants have been developed that are made from bone. Examples of such spacers made from bone having use in spinal procedures are disclosed in U.S. Pat. No. 5,989,289. The spacers in the '289 patent are provided with vertebral engaging surfaces on the upper and lower faces of the implant to resist migration of the implant in the disc space and/or expulsion of the implant from the disc space. While spacers made of bone offer much improved incorporation in fusion procedures, the inherent brittle nature of bone resulting from a high mineral content, particularly load-bearing cortical bone, severely limits its potential for use in applications that require the implant to resist loading other than bearing or compression type loading. For example, cortical bone typically consists of approximately 70% mineral content and 30% non-mineral matter. Of this non-mineral matter, approximately 95% is type I collagen, with the balance being cellular matter and non-collagenous proteins.

Bone grafts have commonly been used in a fixed shape, pulverized, or as pliable demineralized bone. One form of a pliable bone graft is a demineralized bone material typically in the form of a sponge or putty having very little structural integrity. While a demineralized bone segment may retain properties suitable to support bone ingrowth, the structural properties of the bone are altered by removal of its mineral content. Thus, such bone sponges and putties may not typically be used in load-bearing applications.

Therefore, there remains a need for bone implants having the requisite load carrying capabilities for applications that require both bearing or compression load carrying capabilities along with capabilities for resisting loading other than bearing or compression type loading.

SUMMARY OF THE INVENTION

The present invention is directed to a bone implant having a rigid portion for insertion between adjacent bony structures and a flexible portion for securement to the adjacent bony structures.

According to one aspect of the invention, there is provided an implant that has a body portion positionable in the disc space between adjacent upper and lower vertebrae. The implant further includes an upper member and a lower member extending from the body portion along the upper vertebral body and the lower vertebral body, respectively. The body portion, the upper member, and the lower member are each made from bone material.

According to another aspect of the invention, there is provided an implant that includes a bone body with a first bearing surface and a second bearing surface. An upper bone member extends from the body in a first direction and a lower bone member extends from the body in a second direction opposite the first direction. The upper and lower bone members are at least partially demineralized and flexible.

According to a further aspect of the invention, there is provided a spinal fusion implant that is adapted for insertion into the space between adjacent first and second vertebral bodies. The implant includes a bone body having a first bearing surface for contacting an endplate of the first vertebral body and a second bearing surface for contacting the endplate of the second vertebral body. At least one flexible portion extends from the bone body so that it can be secured to one of the first or second vertebral bodies outside the disc space.

According to yet another aspect of the invention, there is provided a method of preparing a bone implant. The method includes providing a rigid bone segment having a body portion with an upper bearing surface and opposite lower bearing surface. The rigid bone segment further includes an upper flange member and an opposite lower flange member that each extend from the body portion. The upper and lower flange members are at least partially demineralized so as to be flexible.

According to another aspect of the invention, there is provided a method of inserting an interbody fusion implant made of bone. The method includes: providing an implant formed of bone and having a body portion with an upper bearing surface and opposite lower bearing surface, the rigid bone segment including a flexible upper flange member and an opposite flexible lower flange member each extending from the body portion; accessing the disc space between adjacent vertebrae; inserting the body portion of the implant into the disc space; securing the flexible upper flange member to the upper vertebra; and securing the flexible lower flange member to the lower vertebra.

According to a further aspect of the invention, a method of preparing a bone implant, is provided. The method includes obtaining a rigid bone segment and forming from the rigid bone segment an implant having a body portion with an upper bearing surface and opposite lower bearing surface, the rigid bone segment further including an upper flange member and an opposite lower flange member each extending from the body portion.

These and other aspects, advantages, features, embodiments, and objects of the present invention will be apparent to those skilled in the art based on the following descriptions of the illustrated embodiments of the present invention.

DESCRIPTION OF THE ILLUSTRATED EMBODIMENTS

Figure 1:
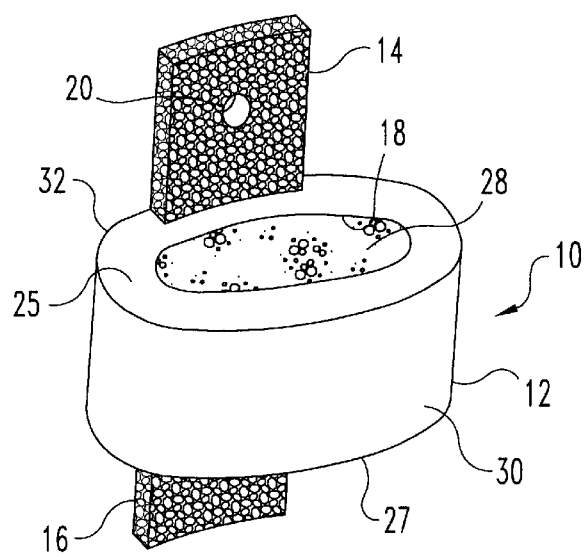
FIG. 1 is perspective view of an implant according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated therein are contemplated as would normally occur to one skilled in the art to which the invention relates.

Referring now to FIG. 1, there is shown an implant according to one embodiment of the present invention. Although implants according to the present invention may have many uses, the embodiment shown in FIG. 1 is particularly adapted for promoting interbody fusion in the spine. Specifically, FIG. 1 illustrates a bone implant 10 having a first substantially rigid body portion 12 that extends between a leading end 30 and a trailing end 32. Implant 10 further includes at trailing end 32 a first or upper flange member 14 that extends upwardly from body portion 12 and a second or lower flange member 16 that extends downwardly from body portion 12. Preferably, body portion 12 and flange members 14, 16 are made from a single piece of bone material, and the flange members are integral with body portion 12. However, other embodiments contemplate that the flanges are made from a separate piece of material, such as bone or cartilage, and secured to body portion 12 via fasteners or other known bonding technique.

Flange members 14 and 16 have been at least partially demineralized to create flexible flange members extending from rigid body portion 12. The demineralized portion of implant 10 can extend through rigid body portion 12 between upper flange member 14 and lower flange member 16 as illustrated. Alternatively the demineralized portion can extend partially into rigid body portion 12, or terminate at the junction between flange members 14, 16 and rigid body portion 12. Preferably, at least flange members 14 and 16 have been completely demineralized to provide maximum flexibility. The flexibility created by demineralization permits flange members 14 and 16 to be movable with respect to rigid body portion 12 and with respect to each other, and thus function similarly to a ligament extending between and secured to the adjacent bony structure and to body portion 12.

Body portion 12 of implant 10 has a cavity 18 which is preferably derived from the intermedullary canal of the bone from which implant 10 is obtained by a cross-cut across the diaphysis of a fibula, femur or like long bone. Cavity 18 provides an area to receive material that promotes bony incorporation and fusion. Prior to positioning body portion 12 into the disc space, bone growth promoting material 28 may be positioned in cavity 18 to encourage bone growth into and through body portion 12. Bone growth material can be any type of material known in the art. As shown further in FIG. 2, upper flange member 14 includes a first fastener bore 20 for receiving a first fastener 24 and lower flange member 16 has a second fastener bore 22 for receiving a second fastener 26. The fasteners of the present invention can be in the form of a threaded screw and made from metal, bone, polymer, bio-absorbable material, or other material known in the art.

Figure 2:
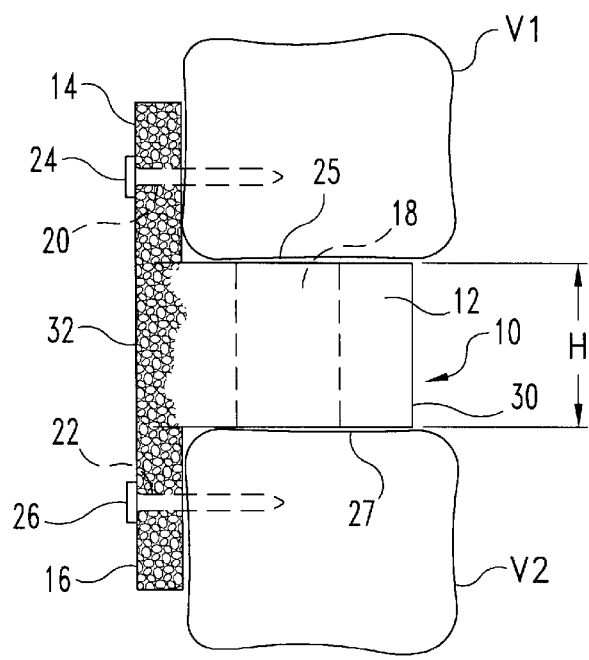
FIG. 2 is a side elevational view of the implant of FIG. 1 inserted in the disc space between adjacent vertebrae.

As shown in FIG. 2, one specific application of the present invention implant 10 contemplates use for fusion of the vertebrae of the cervical spine. In this embodiment implant 10 is obtained from the fibula. Body portion 12 can have any shape, including a specific shape for use in the cervical region, such as those shapes identified in U.S. Pat. No. 5,989,289 which is incorporated herein by reference in its entirety. The vertebrae V1 and V2 are accessed from an anterior approach using known surgical techniques. The disc material is removed and the disc space height is restored, if necessary, using known surgical techniques. Implant 10 is inserted into the prepared disc space. Rigid body portion 12 is adapted to provide structural support between the respective lower endplate of upper vertebra V1 and the upper endplate of vertebra V2. In the illustrated embodiment, rigid body portion 12 has a height H sufficient to provide support for and maintain the desired spacing between adjacent vertebra V1 and V2. Fusion between vertebrae V1 and V2 is obtained with bone growth through cavity 18, which is filled with bone growth material 28. Fusion between the vertebrae can be further promoted by reducing the endplates to bleeding bone prior to insertion of implant 10.

Implant 10 has upper bearing surface 25 that contacts and supports upper vertebral body V1 and lower bearing surface 27 that contacts and supports implant 10 on lower vertebral body V2. Body portion 12 has height H between upper bearing surface 25 and lower bearing surface 27 that is substantially equal to the height of disc space formed between vertebra V1 and vertebra V2. It will understood by those skilled in the art that in the preferred embodiment illustrated herein, the height H is substantially constant. Furthermore, while a uniform height implant is shown in FIG. 2, it will be understood that the implants of the present invention may have a tapered height such that the implant could be utilized for establishing or maintaining the proper curvature in the spine. Rigid body portion 12 has sufficient rigidity and structural integrity to substantially maintain height H and to withstand normal forces applied to the spinal column. Flange members 14 and 16 need not have such structural requirements, although, preferably, each assists in the implant stability by maintaining rigid body portion 12 in the disc space between the two vertebrae.

Fasteners 24 and 26 are placed through the corresponding fastener bores 20 and 22 in the upper and lower flange members 14 and 16, respectively, to stabilize implant 10 in the disc space. Since flange members 14 and 16 are flexible, they can be manipulated and positioned adjacent the vertebral bodies outside the disc space without the creation of large shear and bending stresses in implant 10 at the junction between flange members 14, 16 and body portion 12.

While it is contemplated in one specific embodiment that implant 10 have application for fusion of a cervical region of the spine, application at other regions of the spine and at other joints where it is desirable to have a bone implant with a rigid body portion with a pair of flexible members extending therefrom are also contemplated. Bone implant 10 provides the desirable features of being formed of a highly successful bone fusion material, i.e. natural bone, with the advantages of having flexible members made from bone to secure the rigid bone body portion of the implant at the implantation location.

In another surgical technique, a tensile force can be applied to upper flange member 14 prior to insertion of fastener 24. When fastener 24 is secured to vertebra V1, the tensile force is released. Fastener 26 can be similarly inserted through bore 22 of a tensioned lower flange member 16. The pre-tensioned upper flange member 14 and pre-tensioned lower flange member 16 thus apply a compressive load on body portion 12 in the disc space, further promoting fusion and incorporation of implant 10 and inhibiting expulsion of implant 10 from the disc space.

Figure 3:
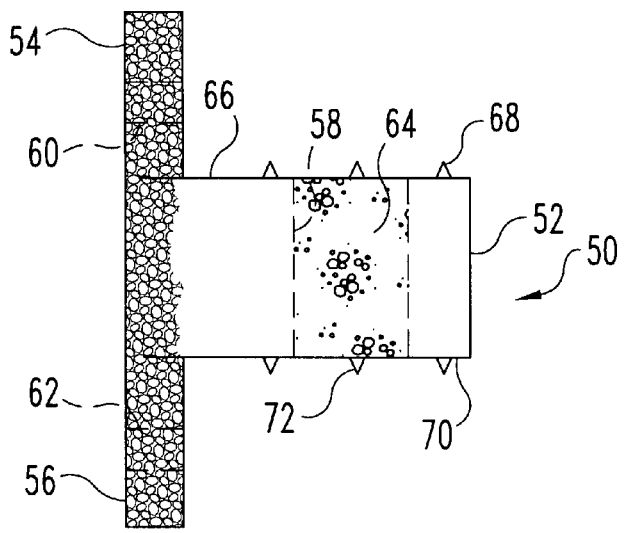
FIG. 3 is a side elevational view of another embodiment implant according to the present invention.

Referring now to FIG. 3, a further embodiment implant is shown and designated as 50. Implant 50 is substantially identical to implant 10. Implant 50 includes rigid body portion 52 with flexible upper flange member 54 and flexible lower flange member 56 extending therefrom. A first fastener bore 60 is formed through upper flange member 54 and a second fastener bore 62 is formed through lower flange member 56. Body portion 52 includes a cavity 58 in which bone growth material 64 is placed.

Body portion 52 further includes a number of upper bone engagement ridges 68 formed on and extending upwardly from upper bearing surface 66 with an identical set of lower ridges 72 formed on and extending downwardly from lower bearing surface 70. It will be understood that while ridges have been shown in the illustrated embodiment, it is contemplated that there are a variety of structures, which could provide a surface for effective engagement with the vertebral bodies to limit expulsion from the disc space. Examples of some such further structures are discussed in U.S. Pat. No. 5,989,289. Further, the endplates or bearing surfaces of the adjacent bony structure can be roughened or otherwise shaped to retain the body portion 52 in its inserted position.

Figure 4:
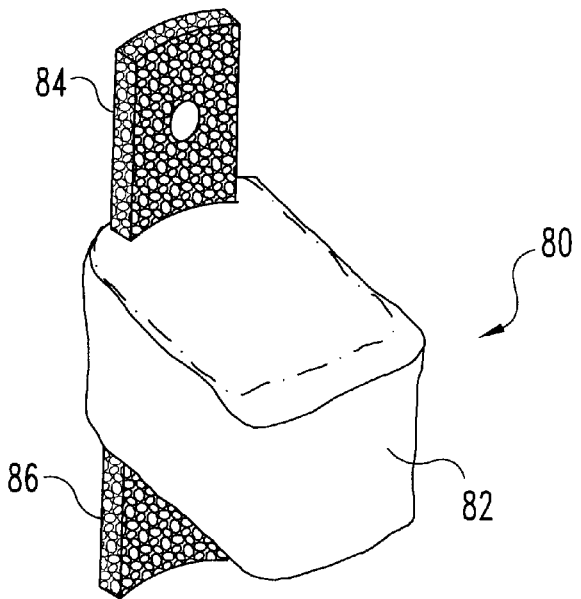
FIG. 4 is a perspective view of yet another embodiment implant according to the present invention.

Referring now to FIG. 4, there is shown another embodiment implant 80 for use in vertebral fusion procedures that has particular application in a posterior approach to the disc space, although implant 80 may be used in other approaches, including anterior and lateral approaches. Implant 80 has a rigid body portion 82 with an upper flange member 84 and a lower flange member 86 each extending from rigid body portion 82 at its trailing end. Implant 80 does not have a cavity and can therefore have a width that is less than the width of implants 10 and 50. Access to the disc space between adjacent vertebra is achieved as known in the art. Examples of such techniques and posterior bone implants are discussed in PCT Publication No. WO 00/24327, which is incorporated herein by reference in its entirety. Once access is achieved, the disc space is distracted if necessary. Implant 80 is moved into the disc space with body portion 82 positioned between the adjacent vertebrae and upper flange member 84 and lower flange member 86 positioned adjacent the vertebral bodies outside the disc space. Once body portion 82 is secured in the disc space D, fasteners can be used to secure the flange members to the respective adjacent vertebral body. It will be understood that a second implant can be placed in the disc space adjacent the first inserted implant to provide further stability.

Although not illustrated, the implants of the present invention can have a slot or threaded bore for engaging a driving tool adapted to position and push the implant into the disc space.

The bone for the implants of present invention is preferably selected from one of the femur, tibia, fibula radius, or ulna or other bone segment having the requisite cortical bone strength. It is further contemplated that implant 10 can be autograft, allograft, or xenograft bone with the bone being treated as known in the art for subsequent implantation into the recipient. Specifically, the bone implant may be selected from donor bone having sufficient resistance to compression between the upper and lower surfaces to find application in the intended environment.

Creation of the demineralized portion of the bone will now be described. The processing involves the use of donor bone with processing in a clean room environment within a bone processing facility. Such donor bone may include allograft from human sources or xenograft from animal sources. Further, it is contemplated that as technology advances in the area of bone processing, the donor bone may be generated in the manufacturing process, either by bone growth or by a processing of constituent components of bone to create artificial materials having properties very similar to bone. More specifically, while any available allogenic or xenogenic bone stock may be utilized for the procedure, cortical bone is conventionally preferred for spinal fusion for its structural properties, although cortical cancellous or cancellous bone may be used depending upon the particular requirements for the implant.

In further processing, the connective tissues are removed and the bone is cleaned, rinsed, and defatted using a solvent such as ethanol or hydrogen peroxide. The bone is then machined or otherwise shaped using conventional techniques to create its final shape. The upper and lower flange members and, if require, the body portion are demineralized to create the required flexible capability. Penetration of the demineralization fluid into the bone adjacent the desired area of flexibility may be controlled by hydrostatic pressure thereby limiting the area of demineralization. The amount of mineral removed from the bone may be adjusted to create the desired amount of flexibility. This demineralization conventionally uses an organic acid such as hydrochloric, nitric, or citric acid. Preferably, the demineralization solution comprises 0.1 to 1.0 N HCl, most preferably 0.3 N HCl. If a xenograft is used, known techniques on the utilization of organic solvents to inactivate bone proteins and reduce antigenecity may be applied at this point. Additionally, the use of glutaraldehyde may take place in order to further cross-line the collagen structure following removal of the mineral portion. Once the implant has been machined and partially demineralized, it may be stored prior to insertion.

Although the above-described processing is disclosed herein as a preferred embodiment, it is contemplated that other suitable processes may be used.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An implant, comprising:
   a body portion positionable in the disc space between adjacent upper and lower vertebrae;
   an upper member extending from said body portion and configured to extend along the body of said upper vertebra; and
   a lower member extending from said body portion and configured to extend along the body of said lower vertebra, wherein said body portion, said upper member, and said lower member are each made from bone material.

2. The implant of claim 1, wherein said upper member and said lower member are each flexible permitting movement of said upper member and said lower members in relation to said body portion.

3. The implant of claim 2, wherein said upper and lower members are made from at least partially demineralized bone.

4. The implant of claim 2, wherein said upper and lower members are made from completely demineralized bone.

5. The implant of claim 1, wherein said body portion includes an upper bearing surface and a lower bearing surface separated by a height, said height adapted to maintain spacing between the adjacent vertebrae.

6. The implant of claim 5, wherein each of said upper and lower bearing surfaces includes a bone engaging surface to inhibit expulsion of the implant from the disc space.

7. The implant of claim 1, wherein said body portion is a spinal fusion device and said body portion is adapted to maintain a desired spacing between the adjacent vertebrae.

8. The implant of claim 7, wherein said upper member and said lower member each have an opening formed therethrough to receive a fastener to secure the upper and lower member to the bodies of the upper and lower vertebrae, respectively.

9. The implant of claim 1, wherein said body portion, said upper member, and said lower member are formed of a single bone segment.

10. The implant of claim 1, wherein said body portion has a cavity allowing bone growth between the upper and lower vertebrae.

11. An implant, comprising:
a bone body extending between a first bearing surface and a second bearing surface; and
an upper bone member extending from said body in a first direction and a lower bone member extending from said body in a second direction opposite said first direction, wherein said upper and lower bone members are at least partially demineralized and are configured to extend along an upper vertebral body and a lower vertebral body, respectively, when said bone body is positioned in a space between the upper vertebral body and the lower vertebral body.

12. The implant of claim 11, wherein said body is a ring shaped bone segment.

13. The implant of claim 11, wherein:
said first bearing surface is adapted to contact an endplate of an upper vertebral body and said second bearing surface is adapted to contact an endplate of an adjacent lower vertebral body; and
said upper bone member extends alongside said upper vertebral body and said lower bone member extends alongside said lower vertebral body.

14. The implant of claim 13, wherein said upper bone member and said lower bone member each have an opening formed therethrough to receive a fastener to secure the implant to the upper and lower vertebral bodies, respectively.

15. The implant of claim 11, wherein:
said bone body is positionable in the disc space between an upper vertebral body and a lower vertebral body; and
said upper and lower members act as a ligament extending between and connecting the upper vertebral body and the lower vertebral body.

16. The implant of claim 11, wherein said implant is formed of a single segment of bone.

17. A spinal fusion implant adapted for insertion into the space between adjacent first and second vertebral bodies, comprising:
a bone body having a first bearing surface for contacting an endplate of the first vertebral body and a second bearing surface for contacting an endplate of the second vertebral body; and
at least one flexible portion extending from the bone body for securement to the first and second vertebral bodies outside the disc space.

18. The spinal fusion implant of claim 17, wherein said at least one flexible portion includes a pair of flexible portions.

19. The spinal fusion implant of claim 18, wherein said flexible portions act as a ligament between said first and second vertebral bodies.

20. The spinal fusion implant of claim 18, wherein the implant has a leading end and an opposite trailing end, and said flexible portions are positioned adjacent said trailing end.

21. The implant of claim 17, wherein said implant is formed from a single segment of bone.

22. A method of preparing a bone implant, comprising:
providing a rigid bone segment having a body portion with an upper bearing surface and an opposite lower bearing surface, said rigid bone segment further including an upper flange member and an opposite lower flange member each extending from said body portion; and
at least partially demineralizing the upper and lower flange members to create a flexible upper flange member and a flexible lower flange member extending from the rigid body portion, wherein said upper and lower flange members are configured to extend along an upper vertebral body and a lower vertebral body, respectively, when said body portion is positioned in a space between the upper vertebral body and the lower vertebral body.

23. The method of claim 22, wherein said at least partially demineralizing includes exposing said rigid upper flange member and said rigid lower flange member to a demineralizing fluid.

24. The method of claim 22, further including limiting contact of the body portion with the demineralizing fluid.

25. The method of claim 24, wherein said limiting utilizes hydrostatic pressure to limit the movement of the demineralizing fluid into the body portion.

26. The method of claim 22, further including forming a bone engaging surface on the upper and lower bearing surfaces of the implant.

27. The method of claim 26, wherein said bone engaging surface is configured to prevent movement of the implant.

28. The method of claim 22, wherein the implant is formed from a single segment of bone.

29. A method of preparing a bone implant, comprising:
obtaining a rigid bone segment; and
forming from said rigid bone segment an implant having a body portion with an upper bearing surface and opposite lower bearing surface, said rigid bone segment further including an upper flange member and an opposite lower flange member each extending from said body portion, wherein said upper and lower flange members are configured to extend along an upper vertebral body and a lower vertebral body, respectively, when said body portion is positioned in a space between the upper vertebral body and the lower vertebral body.

30. The method of claim 29, further comprising at least partially demineralizing the upper and lower flange members to create a flexible upper flange member and a flexible lower flange member extending from the body portion.

31. The method of claim 29, wherein:
the upper and lower bearing surfaces each extend between a leading end and a trailing end of the body portion; and
the upper and lower flange members each extend from the body portion at the trailing end.

32. The method of claim 24, wherein the upper and lower bearing surfaces extend substantially parallel to one another.

33. The method of claim 24, further including forming a bone engaging surface on the upper and lower bearing surfaces of the body portion.

34. The method of claim 29, wherein the implant is formed from a single segment of bone.

* * * * *

(12) EX PARTE REEXAMINATION CERTIFICATE (7448th)
United States Patent
Foley

(10) Number: US 6,562,073 C1
(45) Certificate Issued: Apr. 6, 2010

(54) SPINAL BONE IMPLANT

(75) Inventor: Kevin T. Foley, Germantown, TN (US)

(73) Assignee: Warsaw Orthopedic, Inc., Warsaw, IN (US)

Reexamination Request:
No. 90/010,179, Jun. 27, 2008

Reexamination Certificate for:
Patent No.: 6,562,073
Issued: May 13, 2003
Appl. No.: 09/777,702
Filed: Feb. 6, 2001

(51) Int. Cl.
*A61F 2/44* (2006.01)
*A61F 2/46* (2006.01)
*A61F 2/30* (2006.01)
*A61F 2/28* (2006.01)

(52) U.S. Cl. .................. 623/17.11; 623/17.16
(58) Field of Classification Search ........... None
See application file for complete search history.

(56) References Cited

U.S. PATENT DOCUMENTS

| | | | |
|---|---|---|---|
| 4,349,921 A | 9/1982 | Kuntz | 3/1 |
| 4,599,086 A | 7/1986 | Doty | 623/17 |
| 4,627,853 A | 12/1986 | Campbell et al. | 623/16 |
| 4,892,545 A | 1/1990 | Day et al. | 623/17 |
| 4,946,378 A | 8/1990 | Hirayama et al. | 623/17 |
| 5,011,484 A | 4/1991 | Breard | 606/61 |
| 5,053,049 A | 10/1991 | Campbell | 623/16 |
| 5,085,660 A | 2/1992 | Lin | 606/73 |
| 5,092,866 A * | 3/1992 | Breard et al. | 606/61 |
| 5,092,877 A * | 3/1992 | Pinchuk | 623/1 |
| 5,180,393 A * | 1/1993 | Commarmond | 623/13 |
| 5,423,816 A * | 6/1995 | Lin | 606/61 |
| 5,458,641 A * | 10/1995 | Ramirez Jimenez | 623/17 |
| 5,562,738 A * | 10/1996 | Boyd et al. | 623/17 |
| 5,591,235 A * | 1/1997 | Kuslich | 623/17 |
| 5,609,634 A * | 3/1997 | Voydeville | 623/17 |
| 5,674,296 A * | 10/1997 | Bryan et al. | 623/17 |
| 5,681,310 A * | 10/1997 | Yuan et al. | 606/61 |
| 5,702,449 A * | 12/1997 | McKay | 623/17 |
| 5,713,899 A * | 2/1998 | Marnay et al. | 606/61 |
| 5,725,582 A | 3/1998 | Bevan et al. | 623/17 |
| 5,776,196 A | 7/1998 | Matsuzaki et al. | 623/17 |
| 5,899,939 A | 5/1999 | Boyce et al. | 623/16 |
| 5,916,267 A | 6/1999 | Tienboon | 623/17 |
| 5,989,289 A | 11/1999 | Coates et al. | 623/17 |
| 6,001,130 A | 12/1999 | Bryan et al. | 623/17 |

(Continued)

FOREIGN PATENT DOCUMENTS

| | | |
|---|---|---|
| WO | WO 97/14377 | 4/1997 |
| WO | WO 97/37620 | 10/1997 |
| WO | WO 99/09914 | 3/1999 |
| WO | WO 99/21515 | 5/1999 |
| WO | WO 9938453 | 8/1999 |
| WO | WO 99/38463 | 8/1999 |
| WO | WO 00/40179 | 7/2000 |
| WO | WO 00/54821 | 9/2000 |
| WO | WO 00/74607 | 12/2000 |
| WO | WO 01/06933 | 2/2001 |

OTHER PUBLICATIONS

Obwegeser, J.A., "Bioconvertible Screws Made of Allogenic Cortical Bone for Osteosynthesis Following Sagittal Split Ramus Osteotomy Without Postoperative Immobilisation," Journal of Cranio–Maxillo–Facial Surgery, vol. 22 (1994), pp. 63–75.

*Primary Examiner*—Catherine S. Williams

(57) ABSTRACT

Implantable devices useful for creating bony fusion particularly in intervetebral spinal fusion. The device is formed of bone and has a body portion with an upper flange member and an opposite lower flange member extending from the body portion. The upper and lower flange members are at least partially demineralized to create a flexible ligament extending from the body portion. In one application, the body porton is inserted into a disc space and the flexible ligament is secured to vertebrae on either side of the disc space. Techniques are also disclosed for making the implantable devices and for inserting the implantable device into an intervertebral disc space to promote interbody fusion.

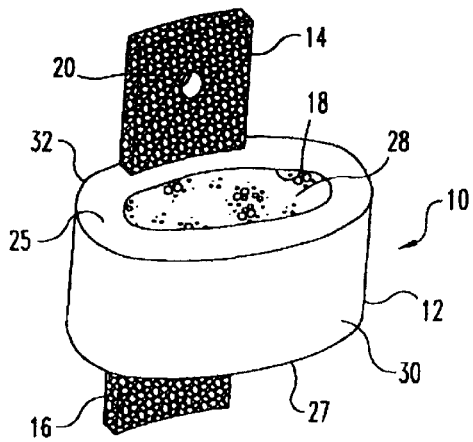

U.S. PATENT DOCUMENTS

| | | |
|---|---|---|
| 6,066,175 A | 5/2000 | Henderson et al. ........ 623/17.11 |
| 6,090,998 A | 7/2000 | Grooms et al. ................ 623/16 |
| 6,093,205 A | 7/2000 | McLeod et al. ................ 623/17 |
| 6,096,081 A | 8/2000 | Grivas et al. ............. 623/17.11 |
| 6,106,527 A | 8/2000 | Wu et al. ...................... 606/61 |
| 6,106,557 A | 8/2000 | Robioneck et al. ............. 623/17 |
| 6,120,503 A | 9/2000 | Michelson .................... 606/61 |
| 6,136,001 A | 10/2000 | Michelson .................... 606/61 |
| 6,156,037 A | 12/2000 | LeHuec et al. ................ 606/61 |
| 6,190,388 B1 | 2/2001 | Michelson et al. ............ 606/61 |
| 6,206,882 B1 | 3/2001 | Cohen .......................... 606/69 |
| 6,206,923 B1 | 3/2001 | Boyd et al. .............. 623/17.11 |
| 6,235,059 B1 | 5/2001 | Benezech et al. ........ 623/17.16 |
| 6,290,718 B1 | 9/2001 | Grooms et al. ................. 623/1 |
| 6,306,170 B2 | 10/2001 | Ray ........................ 623/17.11 |
| 6,325,827 B1 | 12/2001 | Lin ......................... 623/17.16 |
| 6,383,221 B1 | 5/2002 | Scarborough et al. ..... 623/17.11 |
| 6,562,073 B2 | 5/2003 | Foley ...................... 623/17.11 |
| 6,576,017 B2 | 6/2003 | Foley et al. .............. 623/17.16 |
| 6,638,310 B2 | 10/2003 | Lin et al. ................. 623/17.11 |
| 6,652,592 B1 | 11/2003 | Grooms et al. ........... 623/23.51 |
| 2001/0020186 A1 | 9/2001 | Boyce et al. ............. 623/17.16 |
| 2002/0004683 A1 | 1/2002 | Michelson ............... 623/17.16 |
| 2002/0016595 A1 | 2/2002 | Michelson .................... 606/73 |
| 2002/0072806 A1 | 6/2002 | Buskirk et al. ........... 623/23.51 |
| 2002/0107572 A1 | 8/2002 | Foley et al. .............. 623/17.11 |
| 2003/0120274 A1 | 6/2003 | Morris et al. ................. 606/61 |
| 2004/0199253 A1 | 10/2004 | Link et al. .............. 623/17.11 |
| 2004/0199254 A1 | 10/2004 | Louis et al. ............. 623/17.11 |
| 2005/0075634 A1 | 4/2005 | Zucherman et al. ........... 606/61 |

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 11, 17, 22 and 29 are cancelled.

New claims 35–43 are added and determined to be patentable.

Claims 2–10, 12–16, 18–21, 23–28 and 30–34 were not reexamined.

35. *A method of preparing a bone implant comprising:*
   *providing a rigid bone segment having a body portion with an upper bearing surface and an opposite lower bearing surface, said rigid bone segment further including an upper flange member and an opposite lower flange member each extending from said body portion; and*
   *at least partially demineralizing the upper and lower flange menbers to create a flexible upper flange member and a flexible lower flange member extending from the rigid body portion, wherein said upper and lower flange members are configured to extend along and be secured to an upper vertebral body and a lower vertebral body, respectively, in a pre-tensioned state, when said body portion is positioned in a space between the upper vertebral body and the lower vertebral body.*

36. *The method of claim 35, wherein the upper flange member and the lower flange member each have an opening formed therethrough to receive a fastener to secure the upper and lower flange members to the bodies of the upper and lower vertebral bodies, respectively.*

37. *The method of claim 35, wherein said at least partially demineralizing includes exposing the upper flange member and the lower flange member to a demineralizing fluid.*

38. *The method of claim 35, further including limiting contact of the body portion with the demineralizing fluid.*

39. *The method of claim 38, wherein said limiting utilizes hydrostatic pressure to limit the movement of the demineralizing fluid into the body portion.*

40. *The method of claim 38, wherein the upper and lower flange members are separately demineralized such that the dimineralized bone of the upper flange member is not contiguous with the demineralized bone of the lower flange member.*

41. *The method of claim 40, wherein the demineralized bone of the upper and lower flange members extends partially into a section of bone between the upper and lower flanges.*

42. *The method of claim 35, further including forming a bone engaging surface on the upper and lower bearing surfaces of the implant.*

43. *The method of claim 42, wherein said bone engaging surface is configured to prevent movement of the implant.*

* * * * *